United States Patent [19]

Holtkamp

[11] Patent Number: Plant 5,614

[45] Date of Patent: Dec. 31, 1985

[54] AFRICAN VIOLET PLANT NAMED JO

[75] Inventor: Reinhold Holtkamp, Isselburg, Fed. Rep. of Germany

[73] Assignee: Gessellschaftsvertrag uber die Ergindergemeinschaft "Optimara", Fed. Rep. of Germany

[21] Appl. No.: 568,446

[22] Filed: Jan. 5, 1984

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of African violet named Jo characterized by its compact growth habit, relatively small, wavy and serrated girl-type leaves; intense red-purple flower color, profuse flowering, with 7–9 flowers being carried on upright flower stems, and by its long lasting and non-dropping flowers.

1 Drawing Figure

The present invention comprises a new and distinct cultivar of African violet plant, botanically known as *Saintpaulia ionantha,* and named Jo.

The new cultivar was referred to during the breeding and selection process by the designation G 12/X, and is a product of a planned breeding program.

The new cultivar was originated from a cross made in a controlled breeding program in Isselburg, West Germany. The female, or seed parent was a cultivar designated XIX 4158 Red single. The male, or pollen parent was a cultivar designated 67 Red Girl Frilled.

The new cultivar Jo was discovered and selected by me as a flowering plant within the progeny of the stated cross in a controlled environment in Isselburg, West Germany. Asexual reproduction of the new cultivar of leaf cuttings and by division of shoots, as performed by me at Isselburg, West Germany, has demonstrated that the combination of characteristics as herein disclosed for the new cultivar are firmly fixed and are retained through successive generations of asexual reproduction.

Jo has not been observed under all possible environmental conditions. The phenotype may vary significantly with variations in environment such as temperature, light intensity and day length. The following observations, measurements and values describe the new cultivar as grown in Isselburg, West Germany, and Nashville, Tenn. under greenhouse conditions which closely approximate those generally used in commercial practice.

The following traits have been repeatedly observed and are determined to be basic characteristics of Jo, which in combination distinguish this African violet as a new and distinct cultivar:

1. Compact growth habit.
2. Relatively small and wavy leaves which are very serrated at the edges.
3. Seven to nine flower stems, each of which carries flowers which are relatively intensive red purple in flower color.
4. Profuse flowering habit.
5. Long lasting and non-dropping flowers.
6. Leaves are girl type in form, that is, have a relatively bright center.
7. Commercial production is relatively high since the plants can be grown closely adjacent without fear of stretching the leaf petioles.

The accompanying photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural light conditions at approximately 2 P.M. in late November in Nashville, Tenn. When grown under relatively cool finishing conditions, the flower color will be more intensive, and will slightly fade under high finishing conditions.

Botanical classification: *Saintpaulia ionantha,* Ramat. cv. JO.

Parentage:

*Male parent.*—67 Red Girl Frilled.

*Female parent.*—XIX 4158 Red single.

Propagation: The new cultivar holds its distinguishing characteristics through successive propagations by leaf cuttings and by division of shoots.

Plant: From 7 cm. to 9 cm. tall when grown in pots, and approximately 15–18 cm. in diameter when fully grown.

*Leaves.*—General form: Girl type; generally round and wavy, and serrated at the edges. Diameter: 50 mm. Texture: Velvety. Veins: Pronounced. Color (upperside): Yellow green 147A-B, with bright green center. Color (underside): Yellow green 148D. Petiole: Brownish green.

*Flowers.*—Buds: Ball shape. Sepals: Greenish brown, hairy. Calyx: Flat funnel shape. Aspect: Spear shape; hairy. Peduncle: Short upright.

*Individual flowers.*—Size: 30–35 mm. Color: Upperside: Red purple 71 A-B. Underside: Red purple 72A-B. Borne: On upright flower stems, 7–9 flowers per stem. Shape: Violet shape; single to semi-double; frilled and wavy. Flowering time: 10–11 weeks after potting a saleable plant with a fully developed flower head is formed.

*Reproductive organs.*—Anthers: 4 cells, two of which are carried by red purple stems. Filaments: Bright green. Styles: Red-purple with glassy stigma.

*Roots.*—White when young and active; brownish when older.

*Disease resistance.*—Good as experienced to date.

General observations: Jo is a very compact, almost semi-miniature variety having girl type leaves. The plant can be grown nearly pot-tight with other plants without stretching the leaf petioles, thereby resulting in high production. The cultivar flowers profusely, with the flower color being an intensive red-purple, with the compact flower head forming a pleasant contrast with the foliage. The flowers are very long lasting and non-dropping.

I claim:

1. A new and distinct cultivar of African violet named Jo, as described and illustrated, and particularly characterized by its compact growth habit, relatively small, wavy and serrated girl-type leaves; intense red-purple flower color, profuse flowering, with 7–9 flowers being carried on upright flower stems, and by its long lasting and non-dropping flowers.

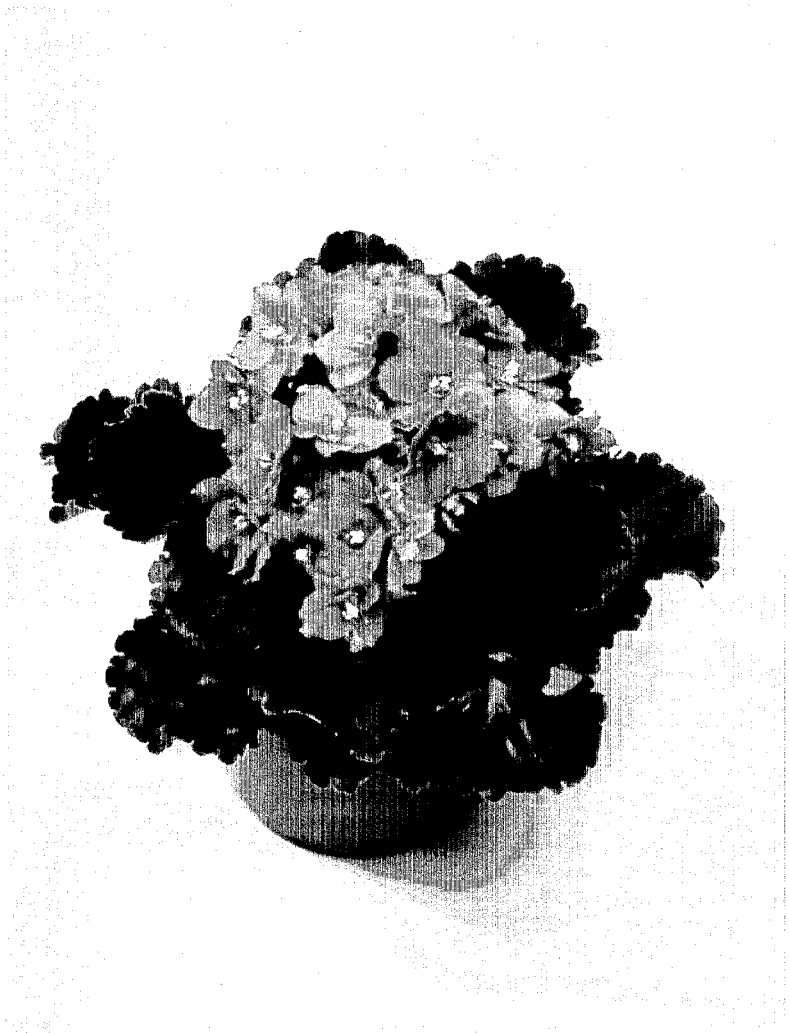

* * * * *